United States Patent [19]

Merianos et al.

[11] Patent Number: 5,008,106

[45] Date of Patent: Apr. 16, 1991

[54] METHOD FOR REDUCING THE MICROBIAL CONTENT OF SURFACES WITH A MICROBIOCIDAL, ANHYDROUS COMPLEX OF PVP-$H_2O_2$

[75] Inventors: John J. Merianos, Middletown; Herbert A. Lieberman, Livingston; Robert B. Login, Oakland, all of N.J.

[73] Assignee: GAF Chemicals Corporation, Wayne, N.J.

[21] Appl. No.: 450,695

[22] Filed: Dec. 14, 1989

[51] Int. Cl.$^5$ .................. A61K 31/79; C01B 15/01
[52] U.S. Cl. ........................... 424/80; 424/43; 424/53; 424/401; 424/433; 424/443; 424/466; 424/616
[58] Field of Search ............... 424/80, 616, 443, 466, 424/433, 401, 43, 53

[56] References Cited

U.S. PATENT DOCUMENTS 2,386,484 10/1945 Levitan ........................... 424/616
3,480,557 11/1969 Shiraeff ........................... 424/62
4,801,460 1/1989 Goertz et al. ..................... 424/80

Primary Examiner—Thurman K. Page
Assistant Examiner—Peter F. Kulkosky
Attorney, Agent, or Firm—Walter Katz; Marilyn J. Maue; Joshua J. Ward

[57] ABSTRACT

What is provided herein is a method for reducing the microbial content of surfaces which comprises contacting said surface with a microbiocidal amount of a substantially anhydrous complex of PVP and $H_2O_2$.

29 Claims, No Drawings

METHOD FOR REDUCING THE MICROBIAL CONTENT OF SURFACES WITH A MICROBIOCIDAL, ANHYDROUS COMPLEX OF PVP-$H_2O_2$

BACKGROUND OF THE INVENTION

1. Field of the Invention

This invention relates to a method for reducing the microbial content of surfaces, and more particularly, to formulations containing an anhydrous complexes of PVP—$H_2O_2$ for treating such surfaces.

2. Description of the Prior Art

Stabilized $H_2O_2$ compositions have found wide utility in commercial and industrial applications, e.g. as antiseptics, disinfectants, sterilization agents, bleaching materials, washing concentrates, etchants, in cosmetic preparations, and as a catalyst in polymerizations requiring a free radical source. In biological applications which require an antiseptic, disinfectant or sterilization agent, such $H_2O_2$ compositions require release of an effective amount of oxygen at a desired rate.

Shiraeff, in U.S. Pat. Nos. 3,376,110 and 3,480,557, discloses a solid, stabilized hydrogen peroxide composition of hydrogen peroxide and a polymeric N-vinyl heterocyclic compound prepared in an aqueous solution of the components. The process involved mixing predetermined amounts of PVP and aqueous $H_2O_2$ and evaporating the solution to dryness. The Shiraeff composition, which was believed to be a solid, dry complex, was described as not necessarily anhydrous due to the hydrophilic nature of the PVP and the water present in the reaction solution. Shiraeff stated that water could be tolerated, however, if it did not affect the solid dry characteristics of the complexes. The $H_2O_2$ content of the composition was given as being at least 2%, and preferably 4.5 to 70% by weight. Prolonged drying of the composition in an attempt to reduce the water content, however, resulted in loss of $H_2O_2$ from the complex, forming a brittle, transparent, gummy, amorphous product of non-reproducible consistency. The resultant hard, brittle chips had a variable $H_2O_2$ content ranging from about 3.20 to 18.07% by weight, depending upon the drying times.

The Shiraeff aqueous PVP—$H_2O_2$ complex did not attain commercial success because (1) the product could not be handled easily because it was not a free-flowing powder; (2) its water and peroxide content of a desired peroxide compound varied over a wide compositional range; (3) the complex had product stability problems; and (4) the laboratory process of preparation could not be scaled up.

An object of the invention is to provide an anhydrous complex of PVP—$H_2O_2$ for reducing the microbial content of surfaces.

Another object of the invention is to provide formulations of anhydrous complexes of PVP—$H_2O_2$ for commercial applications.

Another object of the invention is to provide a method for reducing the microbial content of surfaces with a microbial amount of an anhydrous complex of PVP-$H_2O_2$ having an $H_2O_2$ activity of at least 3%, and, preferably, a molar ratio of PVP to $H_2O_2$ between about 2:1 and 1:1, respectively, corresponding to an $H_2O_2$ content of about 13 to about 24% by weight.

SUMMARY OF THE INVENTION

What is provided herein is a method for preparing a stable PVP and $H_2O_2$ complex and formulations containing it for reducing the microbial content of surfaces, including those which may come into contact with living tissue. This is accomplished by contacting said surface with an antimicrobial amount of a substantially anhydrous complex of PVP and $H_2O_2$.

DETAILED DESCRIPTION OF THE INVENTION

In accordance with the invention, there is provided herein a method and formulations for reducing the microbial content of surfaces with a substantially anhydrous complex of PVP and $H_2O_2$. Suitably, the $H_2O_2$ content of the complex may be as low as 3%, but, preferably, the PVP and $H_2O_2$ constituents of the complex are present in a molar ratio of about 2:1 and 1:1, respectively, corresponding to a $H_2O_2$ content of about 13 and 23% by weight.

The anhydrous PVP-$H_2O_2$ complexes of the invention are prepared by an anhydrous process in an anhydrous organic solvent to provide a predetermined molar ratio of PVP to $H_2O_2$. The product is isolated by filtration of the complex from a suspension in the solvent as a uniform, free-flowing, fine white powder.

The PVP polymeric starting materials used in the present invention are available commercially as a solid of varying molecular weight, water solubility or insolubility, and water content. Typical water soluble PVP polymers are PVP K-15, PVP K-29-32, PVP K-30, K-90 and K-120 (GAF Corp.), which contain less than 5% water. Crospovidone is an example of an available water insoluble PVP material. Mixtures of water soluble and water insoluble PVP also may be used.

In the anhydrous process of the invention for preparing such free-flowing, powder complexes, the PVP powder is suspended in a suitable anhydrous organic solvent, such as a carboxylic acid ester, an alkyl ether, e.g. t-butyl methyl ether, or a hydrocarbon, e.g. cyclohexane. Preferably, however, an alkyl or cycloalkyl ester of a saturated aliphatic carboxylic acid is used, as for example, ethyl acetate, propyl acetate, isopropyl acetate, butyl acetate and ethyl propionate. When the PVP suspension, and $H_2O_2$ solution, in ethyl acetate, for example, is cooled, preferably to about 0° C., a fine, white powder of the desired PVP—$H_2O_2$ complex is precipitated.

An anhydrous $H_2O_2$ solution in an anhydrous organic solvent, preferably the same carboxylic acid ester used to form the PVP suspension, is prepared according to the process of U.S. Pat. No. 4,564,514. In this step, an aqueous $H_2O_2$ solution (e.g. a 50% solution) is treated with the ester and then subjected to azeotropic distillation at a predetermined low pressure, e.g. at 200 mm Hg and 55° C. The resultant product is an anhydrous $H_2O_2$ solution in the ester having a $H_2O_2$ concentration in the range of about 20 to 50% $H_2O_2$.

The thus-prepared anhydrous $H_2O_2$ solution is then slowly added to the cooled PVP suspension in an anhydrous solvent in an amount corresponding to the desired molar ratio of PVP and $H_2O_2$. Preferably, however, a small excess of the $H_2O_2$ solution is used over the desired stoichiometric ratio of reactants. For example, to prepare a PVP—$H_2O_2$ complex having a 1:1 molar ratio of PVP to $H_2O_2$, about 111 g. of PVP and 100 g. of a 42% $H_2O_2$ and 300 ml of anhydrous solvent is used, providing a small excess, e.g. about 5%, over the required stoichiometric amount of 34 g. $H_2O_2$. On a 1:1 molar ratio of $H_2O_2$ to PVP, 34 grams of $H_2O_2$ is required to stoichiometrically react with 111 g. of PVP-K 29-32. The ethyl acetate solvent recovered after filtering the PVP-$H_2O_2$ reaction product has a volume of 160 cc in this example. Therefore, 5% excess of $H_2O_2$ in 160 cc of anhydrous solvent would contain 8 grams of $H_2O_2$. This excess $H_2O_2$ accounts for the use of a 42% rather than a 34% $H_2O_2$ solution of 100 g.

Upon mixing the PVP suspension and anhydrous $H_2O_2$ solution, a fine white powder is obtained immediately which is filtered and dried at about 40°-50° C. in vacuo to remove residual solvent. This product is a stable, anhydrous complex in the form of a uniform, free-flowing, fine white powder having a predetermined $H_2O_2$ content, e.g. between about 13% (2:1 molar ratio) and about 24% $H_2O_2$ (1:1 molar ratio). The water content of the anhydrous PVP-$H_2O_2$ complex is equal to or less than the amount present in the PVP starting material, and usually is less than !%, preferably about 0.5%.

The antimicrobial formulations of the invention are prepared using a microbiocidal amount of the anhydrous PVP-$H_2O_2$ complex, and an acceptable diluent and/or other active and inactive ingredients in the form of a suspension, solution, dispersion gel, powder, paste, suppository, aerosol, ointment, tablet, etc. The formulation may also be impregnated into or applied onto a suitable support, such as a guaze, cotton swab, sponge, etc. Generally, the complex will be activated by water present on the surface containing the microbes, the water functioning to release the active $H_2O_2$ from the complex.

The invention will now be illustrated by the following examples, which should be considered as representative but not limiting of the invention.

EXAMPLE I

Preparation of Anhydrous 1:1 PVP-$H_2$—$O_2$ Complex (23.4% $H_2O_2$)

PVP K-30 (GAF Corp.) (4.5% water), 111 g., was suspended in 200 ml. of anhydrous ethyl acetate (0.01% $H_2O$), and the suspension was cooled to 0° C. An anhydrous hydrogen peroxide solution in ethyl acetate was prepared by treating 200 g. of 50% aqueous hydrogen peroxide with 6 l. of ethyl acetate, and distilling in a rotary evaporator to remove 100 g. of water from the azeotrope solution. A 42.7% $H_2O_2$ solution in anhydrous ethyl acetate was obtained. Then 100 g. of this solution was slowly added over a period of about 1-½ hours to the PVP suspension. A fine white precipitate formed which was filtered and dried in vacuo. The resultant water soluble complex contained 23.4% by weight $H_2O_2$ and 0.5% by weight water, upon drying at 50° C. in vacuo for 2 hours.

EXAMPLE 2

Preparation of Anhydrous 2:1 PVP—$H_2O_2$ Complex (13.2 $H_2O_2$)

The process of Example 1 was followed using 50 g. of the $H_2O_2$ solution in anhydrous ethyl acetate. The resultant anhydrous complex contained 13.2% $H_2O_2$ and 0.5% water.

EXAMPLE 3

Preparation of Water-Soluble, Anhydrous 2:1PVP—$H_2O_2$ Complex (23.1% $H_2O_2$)

200 g. of PVP (K-30) was suspended in 300 g. of anhydrous ethyl acetate. Then 424 g. of anhydrous $H_2O_2$, (19.6% $H_2O_2$ and 0.84% $H_2O$) in ethyl acetate was added in a 45 minutes period to the cooled (5° C.) suspension of PVP/ethyl acetate. This suspension was stirred for an additional 45 minutes, filtered, and washed with anhydrous ethyl acetate. The resultant fine powder was dried under vacuum at 40°-50° C. for 2 hours to recover residual ethyl acetate. The yield was 258.8 g. of water soluble PVP-$H_2O_2$ complex containing 23.1% $H_2O_2$ and 0.4% $H_2O$, which was a free-flowing, white powder. The mother liquor of ethyl acetate, 485 g. contained 4.51% $H_2O_2$.

EXAMPLE 4

Preparation of Water-Insoluble, Anhydrous 2:1 PVP—$H_2O_2$ Complex (24.1% $H_2O_2$)

200 grams of crospovidone XL10 (water-insoluble, cross polymerized PVP) was suspended in 250 g. of anhydrous ethyl acetate. To this suspension 125 g. of anhydrous $H_2O_2$ was added by using 28.1% $H_2O_2$ in anhydrous ethyl acetate and during the addition cooling at 0°-5° C. The resultant, cooled mixture was stirred for an additional 1 hour. The precipitate was filtered to provide 26.2 g. of a water-insoluble, PVP-$H_2O_2$ complex containing 24.1% $H_2O_2$, after drying under vacuum at 40° C. for 2 hours.

EXAMPLE 5

Stability of Anhydrous Complex of Example 1

After 43 days at 60° C. the anhydrous complex of Example 1 lost only 15% of its $H_2O_2$ activity, which demonstrates an excellent stability toward decomposition. At room temperature, decomposition was only 1.5% after 60 days.

| FORMULATION 1 VAGINAL SUPPOSITORY | | |
|---|---|---|
| Ingredient | Percent | Wt. |
| Anhydrous PVP-$H_2O_2$ (23.1%)(Ex.1) | 14.29 | 0.3000 |
| Nonoxynol-9 | 4.76 | 0.1000 |
| Amphoteric-19 | 1.71 | 0.0360 |
| Povidone | 4.29 | 0.0900 |
| Citric acid, anhydrous | 1.93 | 0.0405 |
| Sodium bicarbonate | 3.21 | 0.0675 |
| Polyethylene glycol 1000 | 66.43 | 1.3950 |
| Polyethylene glycol 1540 | 3.38 | 0.0710 |
| | 100.00% | 2.100 |

The suppository dissolves completely in about 1 ml of water in about 10 minutes at a temperature of about 37° C. Upon contact with water, a slight development of foam starts with simultaneous dissolution of the suppository. The foam development increases constantly until the dissolution is complete. The foam which forms has fine pores, is even and remains as such over an extended period of time. The nonoxynol-9 is a spermaticide, and the amphoteric-19 and PVP-peroxide are microbiocides.

FORMULATION 2
EFFERVESCENT MOUTHWASH TABLET

| Ingredient | Percent | Wt. (grams) |
|---|---|---|
| Anhydrous PVP-$H_2O_2$ (23.1%) (Ex.1) | 27.29 | 0.122 |
| Sodium bicarbonate (granular) | 22.4 | 0.100 |
| Sodium carbonate, anhydrous | 2.24 | 0.010 |
| Citric acid, anhydrous (granular) | 44.74 | 0.200 |
| Aminoacetic acid | 1.79 | 0.008 |
| Flavorants (spray dried) | 1.11 | 0.005 |
| Color | 0.22 | 0.001 |
| Sodium benzoate (fine powder) | 0.22 | 0.001 |
| | 100% | 447 mg. |

The tablets are compressed with ⅜-in. diameter, flat-faced, bevel-edge tooling. The tablet ingredients, other than the anhydrous PVP-peroxide complex, are mixed, lightly dampened and granulated. To the slightly dampened granules the anhydrous PVP-peroxide complex is added, and the well-mixed, slightly moist ingredients are compressed, then immediately thereafter placed in a 70° C. forced draft oven for 1 hour to drive off any residual water. The cooled tablets are immediately packaged in air tight aluminum foil pouches.

The tablets are added to 60 cc (2 oz.) of water for use as an effervescent mouthwash and gargle.

FORMULATION 3
NON-AQUEOUS OINTMENT

| Ingredient | Percent | Wt. (g.) |
|---|---|---|
| Anhydrous PVP-$H_2O_2$ (23%) (Ex.1) | 15 | 150 |
| Sorbitan Monopalmitate (Span ® 40-Atlas) | 1 | 10 |
| Polyethylene Glycol 400 Monostearate | 14 | 140 |
| Polyethylene Glycol 400 | 35 | 350 |
| Polyethylene Glycol 4,000 | 35 | 350 |
| | 100% | 1,000 g. |

The polyethylene glycols and the sorbitan monopalmitate are warmed on a water bath to 70° C. and the complex is added to the well-stirred molten mass. Stirring is continued until the ointment is well-solidified.

FORMULATION 4
ANTIBACTERIAL LIPSTICK

| Ingredient | Percent | Wt. (g.) |
|---|---|---|
| Anhydrous PVP-$H_2O_2$ (23%) (Ex. 1) | 15 | 0.30 |
| Polyethylene glycol 1000 | 17 | 0.34 |
| Polyethylene glycol 4000 | 68 | 1.36 |
| | 100% | 2.00 g. |

The formulation is prepared as in 3 above.

FORMULATION 5
POLYETHYLENE GLYCOL-CONTAINING OINTMENT

| Ingredient | Percent | Wt. (g.) |
|---|---|---|
| Anhydrous PVP-$H_2O_2$ (23%) (Ex. 1) | 15.17 | 21 |
| Sodium Carbonate | 5.06 | 7 |
| Polyethylene Glycol 4000 | 36.13 | 50 |
| Polyethylene Glycol 400 | 43.64 | 60.4 |
| | 100% | 138.4 g. |

Heat the polyethylene glycol 4000 and 400 with constant stirring on a water bath at 65° C. Slowly add the micronized anhydrous sodium carbonate and PVP-$H_2O_2$ complex with constant stirring. Cool until the mass is well mixed and congealed.

FORMULATION 6
ANHYDROUS TOOTHPASTE

| No. | Phase | Ingredient | % by Wt. |
|---|---|---|---|
| 1 | E | Anhydrous PVP-Hydrogen Peroxide (23%) (Ex. 1) | 15 |
| 2 | A | Glycerin | 10 |
| 3 | A | Xanthum Gum | 0.25 |
| 4 | B | Polyethylene Glycol 400 | 47 |
| 5 | C | Thixcin | 0.25 |
| 6 | C | Povidone K-90 | 0.5 |
| 7 | D | Monosodium Phosphate | 0.7 |
| 8 | D | Trisodium Phosphate | 1.25 |
| 9 | D | Sodium Saccharin | 0.2 |
| 10 | D | Sodium Fluoride | 0.25 |
| 11 | D | Abrasive Silica | 15 |
| 12 | D | Thickening Silica | 6.6 |
| 13 | D | Titanium Dioxide | 0.5 |
| 14 | D | Sodium Lauryl Sulfate | 1.2 |
| 15 | E | Flavor Oil | 1.2 |
| 16 | E | Pigment | 0.1 |
| | | | 100.0% |

All D items in formula above should be micropulverized and blended. Sprinkle the xanthum gum into glycerin with constant agitation until uniform (Phase A). Add the polyethylene glycol 400 (Phase B) to Phase A with continued agitation. Sprinke in Povidone K-90 until uniform and with constant stirring add the well mixed micronized ingredients of Phase D. Seal unit with cover and apply 28 or more inches of vacuum for 30–45 minutes with continuous agitation. Add all ingredients of phase E, starting with the hydrogen peroxide complex (item 1), under continued agitation and mix until uniform. Mix under vacuum (28 inches or more) for 5 additional minutes.

FORMULATION 7
TOOTH POWDER

| Ingredient | Percent | Wt. (grams) |
|---|---|---|
| Anhydrous PVP-$H_2O_2$ (23%) (Ex. 1) | 15.0 | 15.0 |
| Calcium Sulfate | 52.35 | 52.35 |
| Dicalcium Phosphate | 27.0 | 27.0 |
| Povidone K-90 | 1.5 | 1.5 |
| Sodium Saccharin | 0.15 | 0.15 |
| Sodium Lauryl Sulfate | 3.0 | 3.0 |
| Flavor | 1.0 | 1.0 |
| | 100% | 100 grams |

FORMULATION 8
MEDICATED BANDAGE

| Ingredient | Percent | Wt. (g.) |
|---|---|---|
| Anhydrous PVP-$H_2O_2$ (23%) (Ex. 1) | 14.3 | 100 |
| povidone K-90 | 85.7 | 600 |
| | 100% | 700 g. |

Blend micronized powders of the above two ingredients until homogeneous. Add ethyl alcohol to the well blended powder until a thick homogeneous paste is achieved. Lay a homogeneous layer of 700 mg plus the ethyl alcohol used for dispersion on 1 sq. inch of bandage. Place the coated bandage material under vacuum and heat until the ethyl alcohol is completely evaporated. The resultant mixture of the $H_2O_2$ complex and povidone K-90, evenly spread on 1 square inch of bandage will yield about 3% of available $H_2O_2$ from the solid povidone mixture.

If substantive microbiocidal activity is desired, 0.1% of cetyl pyridinium chloride can be mixed into the above blend before evaporation of the ethyl alcohol.

FORMULATION 9
EAR DROPS SOLUTION

| Ingredient | Percent | Wt. (g.) |
|---|---|---|
| Anhydrous PVP-$H_2O_2$ (23%) (Ex. 1) | 6.5 | 6.5 |
| Anhydrous glycerol | 93.5 | 93.5 |
| | 100% | 100 g. |

FORMULATION 10
SOFT LENS DISINFECTION TABLET

| Ingredient | Percent | Wt. (g.) |
|---|---|---|
| Anhydrous PVP-$H_2O_2$ (23%) (Ex. 1) | 81.5 | 1.50 |
| Sodium bicarbonate (granular) | 5.4 | 0.10 |
| Sodium carbonate, anhydrous | 0.6 | 0.01 |
| Citric acid, anhydrous granular | 10.8 | 0.20 |
| Sodium benzoate (fine powder) | 1.7 | 0.03 |
| | 100% | 1.84 g. |

The tablet ingredients, other than the anhydrous PVP—$H_2O_2$ and sodium benzoate are mixed, lightly dampened to form a damp granule. To the slightly dampened granules to povidone peroxide and sodium benzoate are added so that granules with a damp feel are compressed using 1-¼" flat-faced, bevel-edge punches. Immediately after compression the damp tablets are placed in a 70° C. forced draft oven for 1 hour to drive off any residual water. The cooled tablets are immediately packaged in air-tight aluminum foil pouches.

FORMULATION 11
MEDICATED POWDER

| Ingredient | A | B | C |
|---|---|---|---|
| PVP K-30-$H_2O_2$ (6.47%) (Soluble PVP) | 10 | 50 | 60 |
| PVP-Crospovidone-$H_2O_2$ (23.67%) (Insoluble PVP) | 10 | 1 | 5 |
| Talc | 60 | 45 | 30 |
| PVP K-30 | 10 | — | — |
| Polyplasdone ® XL10 | 10 | 4 | 5 |
| $H_2O_2$ Activity | 3% | 3.5% | 5.0% |

The above powders were mixed together to provide the desired composition.

FORMULATION 12
WOUND DRESSING

| Ingredient | Percent | Wt. (g.) |
|---|---|---|
| Anhydrous PVP-$H_2O_2$ (22.8% $H_2O_2$) | 10 | 10 |
| Absolute Ethanol | 90 | 90 |
| | 100% | 100 g. |

A 1% $H_2O_2$ solution of the above composition is applied to a wound. A film is formed which is effective to disinfect the wound.

FORMULATION 13
COLD WATER LAUNDRY TABLET

| Ingredient | Percent | Wt. (g.) |
|---|---|---|
| PVP-$H_2O_2$ (23%) (Ex. 1) | 81.5 | 1.50 |
| Sodium benzoate (fine powder) | 1.64 | 0.03 |
| | 100% | 1.84 g. |

These anhydrous PVP—$H_2O_2$ tablets are an effective cold water bleach-disinfectant for cleaning clothes, etc. In use, the PVP portion of the complex can chelate with inorganic ions (e.g. $Ca^{++}$, $Mg^{++}$) in the water to reduce water hardness. It can also provide laundry detergents with the properties of antiredeposition or suspension of dirt, anti-dye transfer, along with its bleaching and disinfectant action.

FORMULATION 14
WATER DISINFECTANT TABLET

| Ingredient | Percent | Wt. (g.) |
|---|---|---|
| Sodium bicarbonate | 6.3 | 0.10 |
| Sodium carbonate, anhydrous | 0.6 | 0.01 |
| Citric Acid, anhydrous granules | 12.6 | 0.20 |
| Povidone-$H_2O_2$ (20%) | 78.6 | 1.25 |
| Sodium benzoate (fine powder) | 1.9 | 0.03 |
| | 100.0% | 1.59 g. |

This tablet should be dissolved in one quart of water and allowed to remain for 5 minutes after the tablet is dissolved before the water is ready to drink. To prepare the tablet, follow the same directions as given in Formulation 10 except use a 1 inch flat-faced, bevel-edge punch.

The above formulations and applications illustrate methods of reducing the bacterial content of surfaces using the anhydrous PVP-$H_2O_2$ complex of the invention. It is to be understood, however, that the above examples are provided to illustrate specific and preferred embodiments of the invention and that many modifications and alterations can be made in these examples without departing from the scope of the invention.

What is claimed is:

1. A method for reducing the microbial content of surfaces which comprises contacting said surface with a microbiocidal amount of a stable complex of PVP and $H_2O_2$ containing between about 3 and 24% by weight of $H_2O_2$ in an anhydrous organic solvent which is obtained directly as a uniform, free-flowing, fine white powder by reaction between PVP and $H_2O_2$ in substantially the same weight ratio as predetermined for the complex.

2. A method according to claim 1 wherein said complex has an $H_2O_2$ content of about —to 24% by weight.

3. A method according to claim 1 wherein said complex has a molar ratio of PVP and $H_2O_2$ between about 2:1 and about 1:1.

4. A method according to claim 1 wherein said complex is present in a formulation in an amount of about 0.1 to 15% by weight.

5. A method according to claim 1 wherein said complex is present in a suspension, solution, suppository, gel, powder, paste, ointment, or tablet.

6. A method according to claim 1 wherein said complex is present on a support.

7. A method according to claim 1 wherein said support is a gauze, cotton swab or sponge.

8. A method according to claim 1 wherein said complex is present in a non-aqueous formulation.

9. A method according to claim 1 wherein said surface comes into contact with living tissue.

10. A formulation for reducing the microbial content of surfaces which include a microbiocidal amount of an the PVP and $H_2O_2$ complex of claim 1.

11. A formulation according to claim 10 wherein the complex has an $H_2O_2$ content of about 3 to 24% by weight.

12. A formulation according to claim 10 wherein the complex has a molar ratio of PVP and $H_2O_2$ between about 2:1 and about 1:1.

13. A formulation according to claim 10 which also includes one or more of an acceptable diluent, and an active or inactive ingredient.

14. A formulation according to claim 10 which is in the form of a suspension, solution, suppository, gel, powder, paste, ointment, or tablet, optionally, on a support.

15. A formulation according to claim 10 which is a non-aqueous composition.

16. A formulation according to claim 10 which is a vaginal suppository.

17. A formulation according to claim 10 which is an effervescent mouthwash.

18. A formulation according to claim 10 which is a non-aqueous ointment.

19. A formulation according to claim 10 which is a polyethylene glycol-containing ointment.

20. A formulation according to claim 10 which is an anhydrous toothpaste.

21. A formulation according to claim 10 which is a tooth powder.

22. A formulation according to claim 10 which is a medicated bandage.

23. A formulation according to claim 10 which is an ear drop solution.

24. A formulation according to claim 10 which is a soft lens disinfectant tablet.

25. A formulation according to claim 10 which is a medicated powder.

26. A formulation according to claim 10 which is a wound dressing.

27. A formulation according to claim 10 which is a cold water laundry tablet.

28. A formulation according to claim 10 which is a water disinfectant tablet.

29. A process for reducing the microbial content of surfaces which comprises contacting said surface in the presence of water with a microbial amount of an the complex of PVP and $H_2O_2$ of claim 1.

* * * * *